(12) United States Patent
Voskoboynikov et al.

(10) Patent No.: US 10,856,804 B2
(45) Date of Patent: *Dec. 8, 2020

(54) PUMP HOMEOSTASIS INDICATOR (PHI)

(71) Applicant: HeartWare, Inc., Miami Lakes, FL (US)

(72) Inventors: Neil Voskoboynikov, Pembroke Pines, FL (US); Veronica Ramos, Homestead, FL (US)

(73) Assignee: HeartWare, Inc., Miami Lakes, FL (US)

(*) Notice: Subject to any disclaimer, the term of this patent is extended or adjusted under 35 U.S.C. 154(b) by 227 days.

This patent is subject to a terminal disclaimer.

(21) Appl. No.: 16/026,760

(22) Filed: Jul. 3, 2018

(65) Prior Publication Data

US 2019/0015040 A1 Jan. 17, 2019

Related U.S. Application Data

(60) Provisional application No. 62/531,960, filed on Jul. 13, 2017.

(51) Int. Cl.
| | |
|---|---|
| *A61M 1/12* | (2006.01) |
| *A61B 5/00* | (2006.01) |
| *A61M 1/10* | (2006.01) |
| *A61B 5/02* | (2006.01) |
| *A61B 5/024* | (2006.01) |

(52) U.S. Cl.
CPC ........ *A61B 5/4851* (2013.01); *A61B 5/02007* (2013.01); *A61B 5/02028* (2013.01); *A61B 5/02042* (2013.01); *A61B 5/02405* (2013.01); *A61B 5/7278* (2013.01); *A61B 5/746* (2013.01); *A61M 1/101* (2013.01); *A61M 1/1086* (2013.01); *A61M 2205/04* (2013.01); *A61M 2205/18* (2013.01); *A61M 2205/3365* (2013.01)

(58) Field of Classification Search
None
See application file for complete search history.

(56) References Cited

U.S. PATENT DOCUMENTS

| | | | |
|---|---|---|---|
| 7,997,854 | B2 | 8/2011 | LaRose et al. |
| 8,419,609 | B2 | 4/2013 | Shambaugh, Jr. et al. |
| 10,561,774 | B2 * | 2/2020 | Voskoboynikov .... A61M 1/122 |

(Continued)

FOREIGN PATENT DOCUMENTS

| | | |
|---|---|---|
| WO | 03057013 A2 | 7/2003 |
| WO | 2015183922 A1 | 12/2015 |

OTHER PUBLICATIONS

International Search Report and Written Opinion dated Oct. 9, 2018, for corresponding International Application No. PCT/US2018/040747; International Filing Date: Jul. 3, 2018 consisting of 10-pages.

*Primary Examiner* — Erica S Lee
(74) *Attorney, Agent, or Firm* — Christopher & Weisberg, P.A.

(57) ABSTRACT

A method determining adverse events from operation of an implantable blood pump including calculating a moving average convergence divergence (MACD) based on power consumed by the implantable blood pump to maintain a constant rotational speed of an impeller of the implantable blood pump. An alert is generated when the calculated MACD diverges from a predetermined MACD threshold and a predetermined MACD zero-crossing time threshold.

16 Claims, 8 Drawing Sheets

(56) References Cited

U.S. PATENT DOCUMENTS

2017/0215261 A1* 7/2017 Potucek .................... E04H 4/12
2018/0024578 A1* 1/2018 Ahuja ..................... G06F 1/206
                                                        700/300

* cited by examiner

PUMP HOMEOSTASIS INDICATOR (PHI)

CROSS-REFERENCE TO RELATED APPLICATION

This application is related to and claims priority to U.S. Provisional Patent Application Ser. No. 62/531,960, filed Jul. 13, 2017, entitled PUMP HOMEOSTASIS INDICATOR (PHI), the entirety of which is incorporated herein by reference.

STATEMENT REGARDING FEDERALLY SPONSORED RESEARCH OR DEVELOPMENT n/a

TECHNICAL FIELD

This disclosure relates to a method and system for determining adverse events from operation of an implantable blood pump.

BACKGROUND

Ventricular assist devices, or VADs, are lifesaving mechanical circulatory support devices, or MCSDs, configured to assist the heart in pumping blood throughout the body. VADs may include centrifugal pumps, axial pumps, or other kinds electromagnetic pumps configured to pump blood from the heart to blood vessels to circulate around the body. One such centrifugal pump is the HVAD sold by HeartWare, Inc. and is shown and described in U.S. Pat. No. 7,997,854 the entirety of which is incorporated by reference. One such axial pump is the MVAD sold by HeartWare, Inc. and is shown and described in U.S. Pat. No. 8,419,609 the entirety of which is incorporated herein by reference.

Detecting patient adverse events associated with the implantation of VADs is challenging owing to the fact that patients requiring such devices often have different cardiac pathology that necessitated the implantation of the VAD within the patient. One solution devised is to implant sensors into or onto the VAD to detect operating parameters of the blood pump. Implanting sensors within or onto VADS, however, requires sensor calibration, are subject to potential failure from corrosion or other events, and increases the power necessary to operate the VAD.

SUMMARY

Some embodiments advantageously provide a method determining adverse events from operation of an implantable blood pump including calculating a moving average convergence divergence (MACD) based on power consumed by the implantable blood pump to maintain a constant rotational speed of an impeller of the implantable blood pump. An alert is generated when the calculated MACD diverges from a predetermined MACD threshold and a predetermined MACD zero-crossing time threshold.

In another aspect of this embodiment, calculating the MACD includes calculating a slow moving average (SMA), and wherein the SMA is an average measurement of the power consumed by the implantable blood measured at a predetermined interval for a first predetermined period of time.

In another aspect of this embodiment, the predetermined interval is 15 minutes.

In another aspect of this embodiment, the first predetermined period of time is 48 hours.

In another aspect of this embodiment, calculating the MACD includes calculating a fast moving average (FMA), and wherein the FMA is an average measurement of the power consumed by the implantable blood measured at the predetermined interval for a second predetermined period of time less the first period of time.

In another aspect of this embodiment, the second predetermined period of time is four hours.

In another aspect of this embodiment, the predetermined MACD threshold is at least one from the group consisting of a minimum MACD value and a maximum MACD value over a continuous 48 hour period multiplied by 150%.

In another aspect of this embodiment, the predetermined MACD zero-crossing time threshold is 24 hours.

In another aspect of this embodiment, the alert is generated at a time of the later of the occurrence of: when the calculated MACD diverges from a predetermined MACD threshold and when the calculated MACD exceeds a predetermined MACD zero-crossing time threshold.

In another aspect of this embodiment, the method further includes clearing the alert when the MACD crosses a zero line of the MACD.

In another aspect of this embodiment, the method further includes calculating a first average power consumed by the implantable blood pump measured at a predetermined interval for a third predetermined period of time. A second average power consumed by the implantable blood pump measured at the predetermined interval for a fourth predetermined period of time greater than the first period of time is calculated. The alert is generated when the calculated first average power consumed by the implantable blood pump deviates from the calculated second average power consumed by the implantable blood pump by two standard deviations.

In another aspect of this embodiment, the third predetermined period of time is three hours.

In another aspect of this embodiment, the fourth predetermined period of time is five days.

In another aspect of this embodiment, the method further includes clearing the alert when the first average power consumed by the implantable blood pump converges to the calculated second average power consumed by the implantable blood pump by less than two standard deviations.

In another aspect of this embodiment, generating the alert is indicative of at least one from the group consisting of thrombus, gastrointestinal bleeding, tachycardia, arrhythmia, and right heart failure.

In another embodiment, a method of determining adverse events from operation of an implantable blood pump includes calculating a first average power consumed by the implantable blood pump to maintain a constant rotational speed of an impeller of the implantable blood pump measured at a predetermined interval for a first predetermined period of time. A second average power consumed by the implantable blood pump to maintain a constant rotational speed of an impeller of the implantable blood pump measured at the predetermined interval for a second predetermined period of time greater than the first period of time is calculated. An alert is generated when the calculated first average power consumed by the implantable blood pump deviates from the calculated second average power consumed by the implantable blood pump by two standard deviations.

In another aspect of this embodiment, the method further includes clearing the alert when the first average power consumed by the implantable blood pump converges to the calculated second average power consumed by the implantable blood pump by less than two standard deviations.

In another aspect of this embodiment, generating the alert is indicative of at least one from the group consisting of thrombus, gastrointestinal bleeding, tachycardia, arrhythmia, and right heart failure.

In another aspect of this embodiment, the first predetermined period of time is between 1-3 hours and the second predetermined period of time is between 1-5 days.

In another embodiment, a system for determining adverse events from operation of an implantable blood pump includes a controller having a processor, the controller being in communication with the implantable blood pump and a power source configured to provide power to the implantable blood pump, the controller being configured to calculate a moving average convergence divergence (MACD) based on power consumed by the implantable blood pump to maintain a constant rotational speed of an impeller of the implantable blood pump and generate an alert when the calculated MACD diverges from a predetermined MACD threshold and exceeds a predetermined MACD zero-crossing time threshold.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
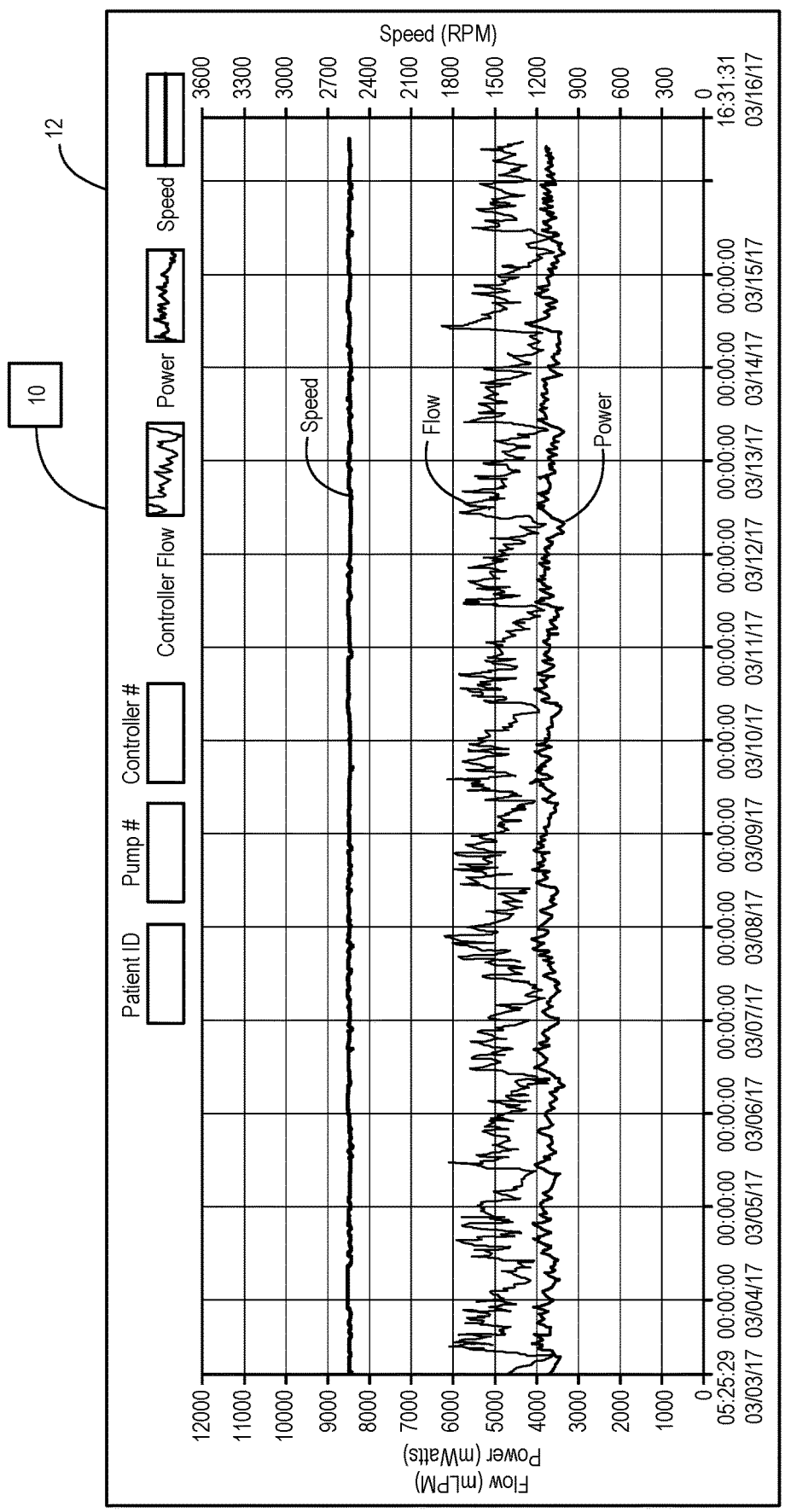
FIG. 1 is an exemplary display of a log file of an implantable blood pump operating within normal parameters.

Before describing in detail exemplary embodiments, it is noted that the embodiments reside primarily in combinations of apparatus components and processing steps related to determining adverse events in a patient with an operating implantable blood pump. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements.

Referring now to the drawings in which like reference designators refer to like elements, there is shown in FIG. 1 an exemplary controller having processor and processing circuity configured to measure parameters of a blood pump implanted within a human or animal patient and to control the operation of the implantable blood pump and designated generally as "10." As used herein, an implantable blood pump refers to any MCSD, such as HVAD, and MVAD, having movable element, such as impeller, configured to pump blood from the heart to the patient's circulatory system. The controller 10 be may in communication with the implantable blood pump through one or more conductors (not shown) and measures parameters such as flow rate out of the pump in mL/pin, power consumption in mWatts, and the rotational speed of the impeller in RPM. The controller 10 is configured to measure a one second average these parameters at a predetermined interval and record these parameters in controller log files 12 stored in the controller 10. For example, in the log file 12 shown in FIG. 1, the controller 10 averages flow rate, power, and speed of the impeller by average the measurement of each parameter over a one second interval every 15 minutes and records the same on the log file 12 which can be displayed in graphical form on a computer as shown in the exemplary log file 12 in FIG. 1. The 15 minute interval may be variable as well as the one second average. For example, it is fully contemplated that any interval, for example, 1-60 minutes may be used to sample the measured parameters from the blood pump and the average may be over, for example, 1-5 seconds. Measuring the one second average of the measured parameters every 15 min helps to reduce noise in the log file 12.

Figure 2:
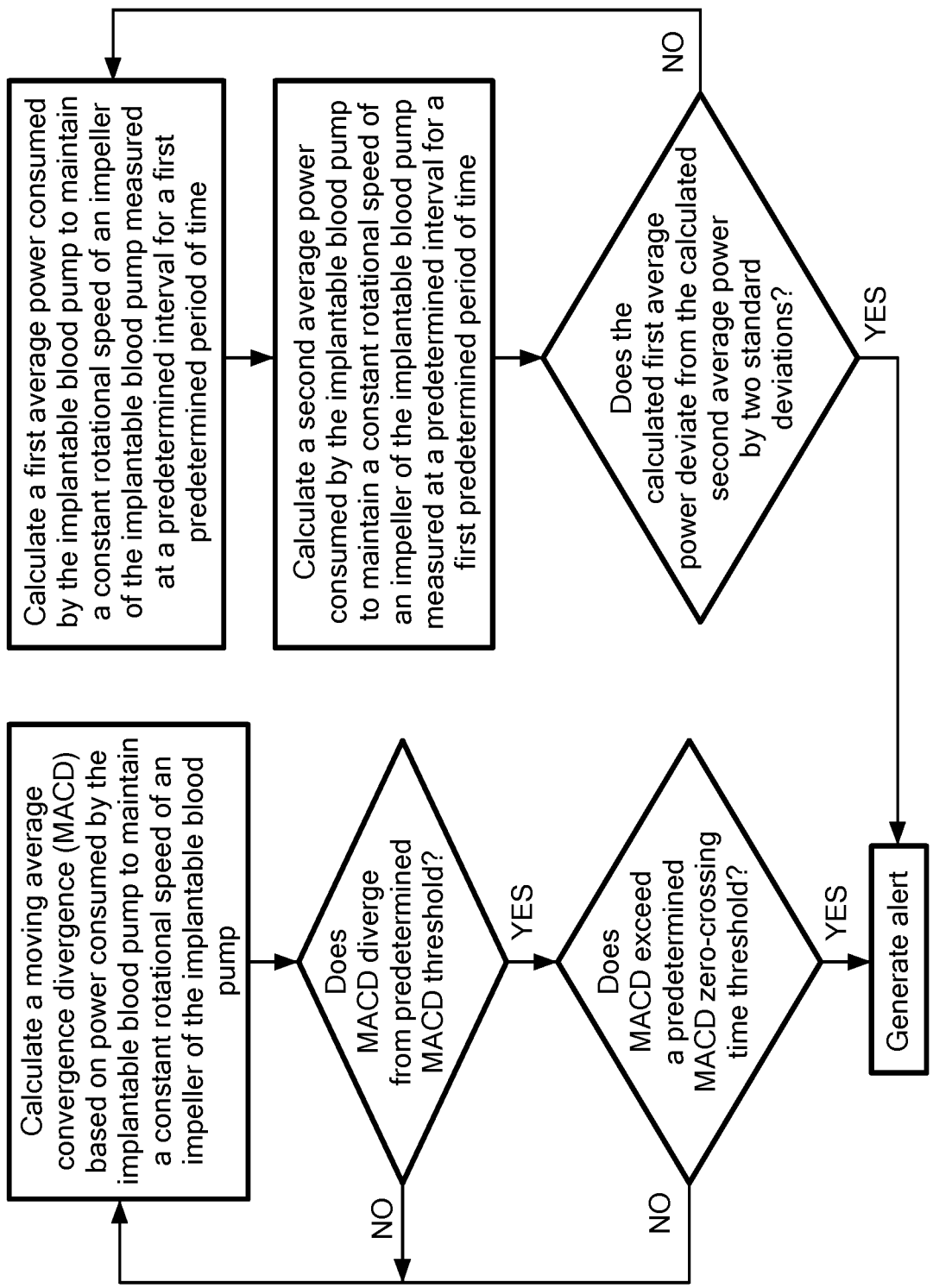
FIG. 2 is an exemplary flow chart showing a method of determining adverse events in a patient with an operating blood pump in accordance with the present application.

Referring now to FIG. 2, the controller 10 is further configured to calculate a moving average convergence divergence (MACD) based on power consumed by the implantable blood pump to maintain a constant rotational speed of an impeller of the implantable blood pump. As used here, the MACD refers a trend-following indicator that shows the relationship between two moving averages of the same parameter. In the exemplary embodiment shown in FIG. 2, calculating the MACD includes calculating a slow moving average (SMA) and a fast moving average (FMA). The SMA is an average measurement, for example over one second of time, of the power consumed by the implantable blood measured at a predetermined interval for a first predetermined period of time. In an exemplary configuration, the predetermined interval for the SMA is 15 minutes and the first predetermined period of time of 48 hours. In other configurations, the first predetermined period of time maybe be longer or shorter than 48 hours. The FMA is a measurement, for example over one second of time, of the power consumed by the implantable blood measured at the predetermined interval for a second predetermined period of time less the first period of time. For example, the FMA may be calculated over the predetermined interval of 15 minutes and for a second period of time of four hours. The one-second average is an exemplary low-pass filter, other low pass filters known in the art are contemplated. The MACD is calculated by subtracting the SMA from FMA to create an index showing trends in power consumed by the implantable blood pump. When the calculated MACD diverges from a predetermined MACD threshold and exceeds a predetermined MACD zero-crossing time threshold an alert may be generated by the controller 10. For example, the method calculates a minimum and a maximum value of the MACD when subtracting the SMA from FMA. The MACD threshold is set as either the minimum or maximum value of the MACD over the prior 48 hour period multiplied by a threshold percentage, for example, 150%. For example, if the maximum MACD value over the prior 48 hour period is 1 then an MACD value of 1.5 would indicate a divergence from the MACD by the predetermined MACD threshold and is indicative that the implantable blood pump is not at homeostasis and is operating abnormally. The MACD threshold may be recorded in the log file and displayed along the MACD signal line.

Continuing to refer to FIG. 2, the controller 10 further determines if there have been any crossings of the zero line of the MACD calculation over an immediately preceding time period. For example, the MACD moves around the zero line as shown in FIG. 1. If the MACD does not cross the zero line for a period of time, for example, 24 hours, and the MACD diverges from the predetermined MACD threshold, then an alert is generated by the controller 10 and displayed in the log file with, for example, the time and date of the alert. In an exemplary configuration, the alert is generated only when both of the MACD diverges from the MACD threshold and when there are no zero crossings for an immediately preceding time period. In other configurations, either the MACD diverging from the MACD threshold or no zero crossings for an immediately preceding time period may trigger the alert. Optionally, an audible and/or visual alarm may be triggered by the controller 10 such that the patient is alerted and may head to a physician for diagnosis of the adverse event.

Continuing to refer to FIG. 2, the controller 10 is further configured to detect outliers in the measured consumption of power concurrently with the calculating of power consumption trends in the form of the MACD index discussed above. In particular, the controller 10 calculates a first average power consumed by the implantable blood pump measured at a predetermined interval for a third predetermined period of time. For example, the third predetermined period of time may be, for example, 3 hours or anywhere from 1-5 hours and the predetermined interval may be 15 minutes. The controller 10 further calculates a second average power consumed by the implantable blood pump measured at the same predetermined interval for a fourth predetermined period of time greater than the first period of time. For example, the fourth predetermined period of time may be, for example, 5 days or anywhere from 1-5 days. When the calculated first average power consumed by the implantable blood pump deviates from the calculated second average power consumed by the implantable blood pump by two standard deviations of the slow moving average the controller 10 generates and alert.

Figure 3:
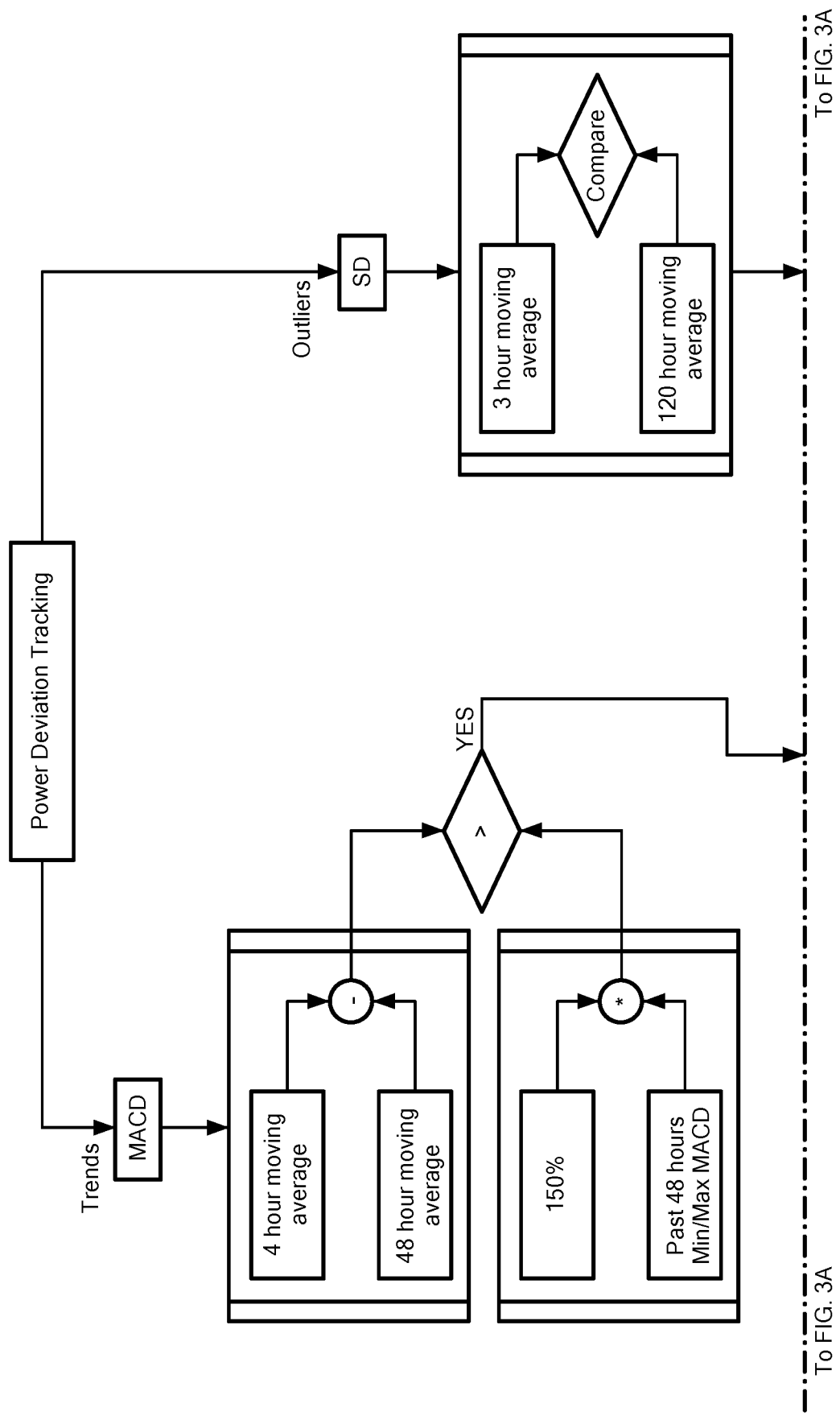
FIG. 3 is the flow chart of FIG. 2 showing features of the method of determining adverse events.
Figure 3A:
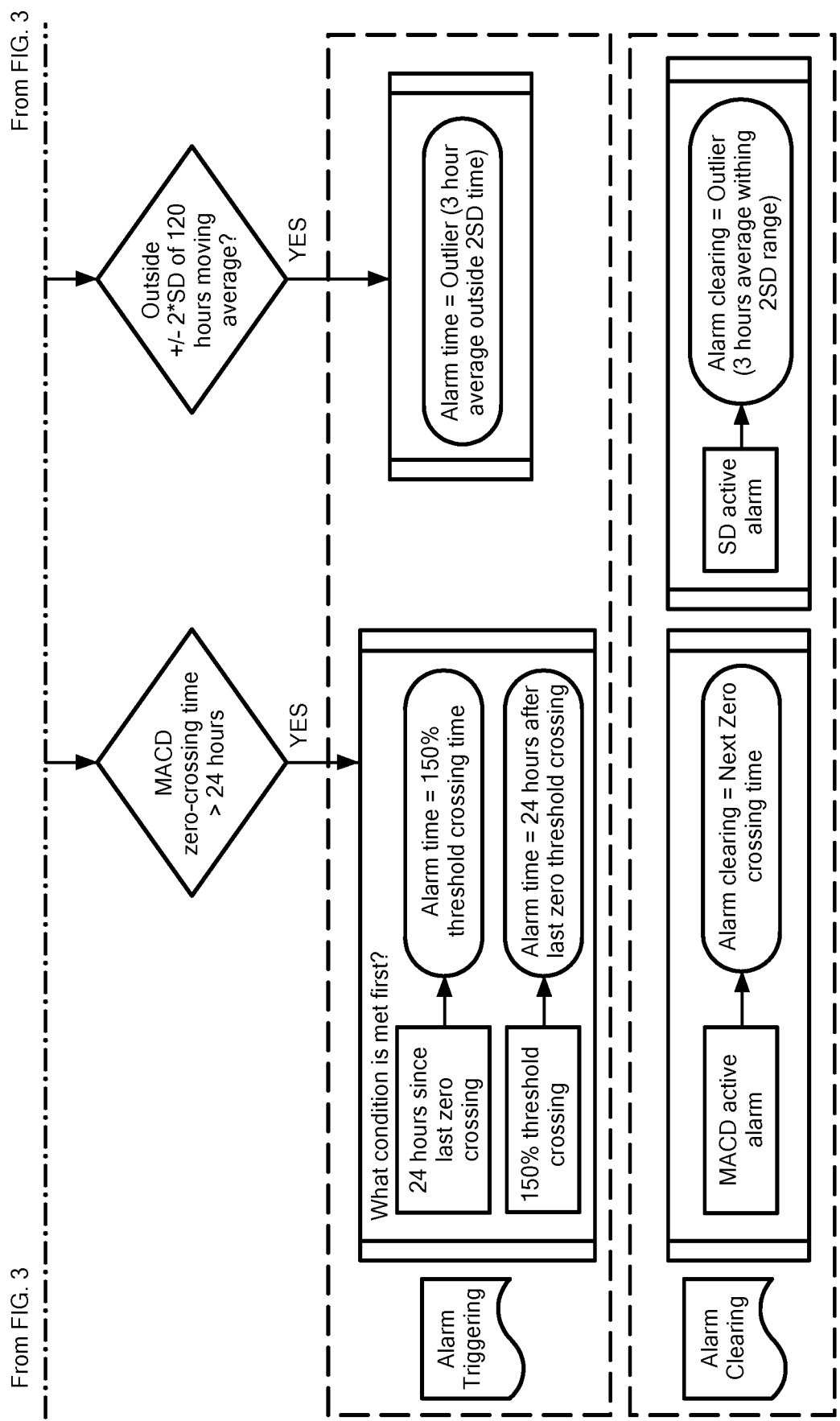
FIG. 3A is the flow chart of FIG. 3 showing when the alert is triggered and when the alert is cleared.

Referring now to FIGS. 3 and 3A, the alert based on divergence of the calculated MACD from is generated at a time of the later of the occurrence of when the calculated MACD diverges from a predetermined MACD threshold when the calculated MACD exceeds a predetermined MACD zero-crossing time threshold. Similarly, the alert is generated when the calculated first average power consumed by the implantable blood pump deviates from the calculated second average power consumed by the implantable blood pump by two standard deviations. The alert may be cleared by the controller 10 when either the calculated MACD crosses the zero line or when the 3 hour power average returns two with two standard deviations of the 5 day power average.

Figure 4:
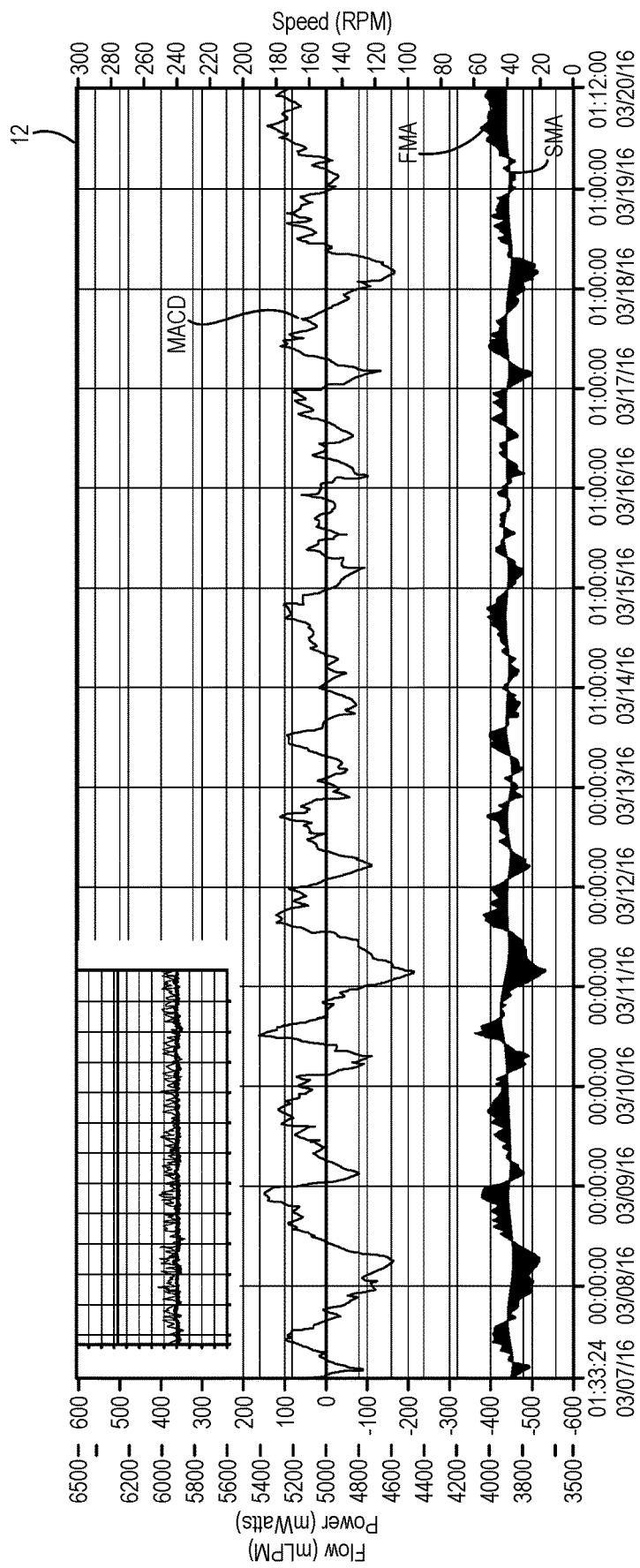
FIG. 4 is an exemplary display of a log file of an implantable blood pump operating in patient with an MACD calculation displayed and operating within normal parameters.

Referring now to FIG. 4, in this exemplary log file 12 of a patient whose pump is operating in homeostasis, the MACD is displayed above the SMA and FMA trend lines and shows a smooth trend line where power increases during that day and decreases at night. The original log file is displayed in the upper corner of the log file 12 with the MACD calculations. The MACD further crosses the zero line at least once every 24 hours and there are no points of the MACD which exceed 150% of the maximum or minimum MACD value for a preceding 48 hour period. Thus, in this exemplary log file 12 no alert was generated and there is no indication of adverse events.

Figure 5:
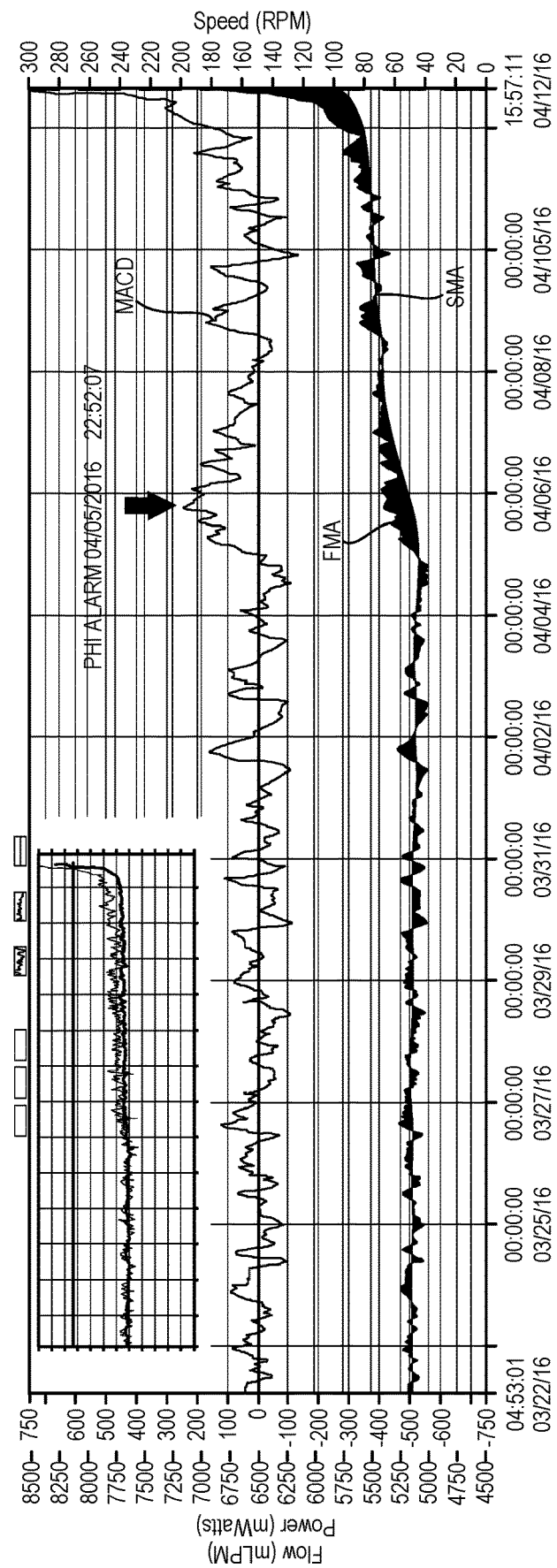
FIG. 5 is an exemplary display of a log file of an implantable blood pump operating within a patient with an MACD calculation displayed and indicating the presence of thrombus.

Referring now to FIG. 5, in this exemplary log file 12 of a patient whose pump is operating is not operating homeostasis, the MACD is displayed above the SMA and FMA trend lines. The original log file is displayed in the upper corner of the log file 12 with the MACD calculations. The MACD does not crosses the zero line between April 5 and April 6 and the MACD exceeds 150% of the maximum or minimum MACD value for the preceding 48 hour period. Thus, in this exemplary log file 12 an alert was generated at the latter of those two events. Such an example is indicative of thrombus as the power increases when the power should be decreasing at night. The above described algorithm for detecting trends and outliers is effective at detecting approximately 99% of thrombus conditions.

Figure 6:
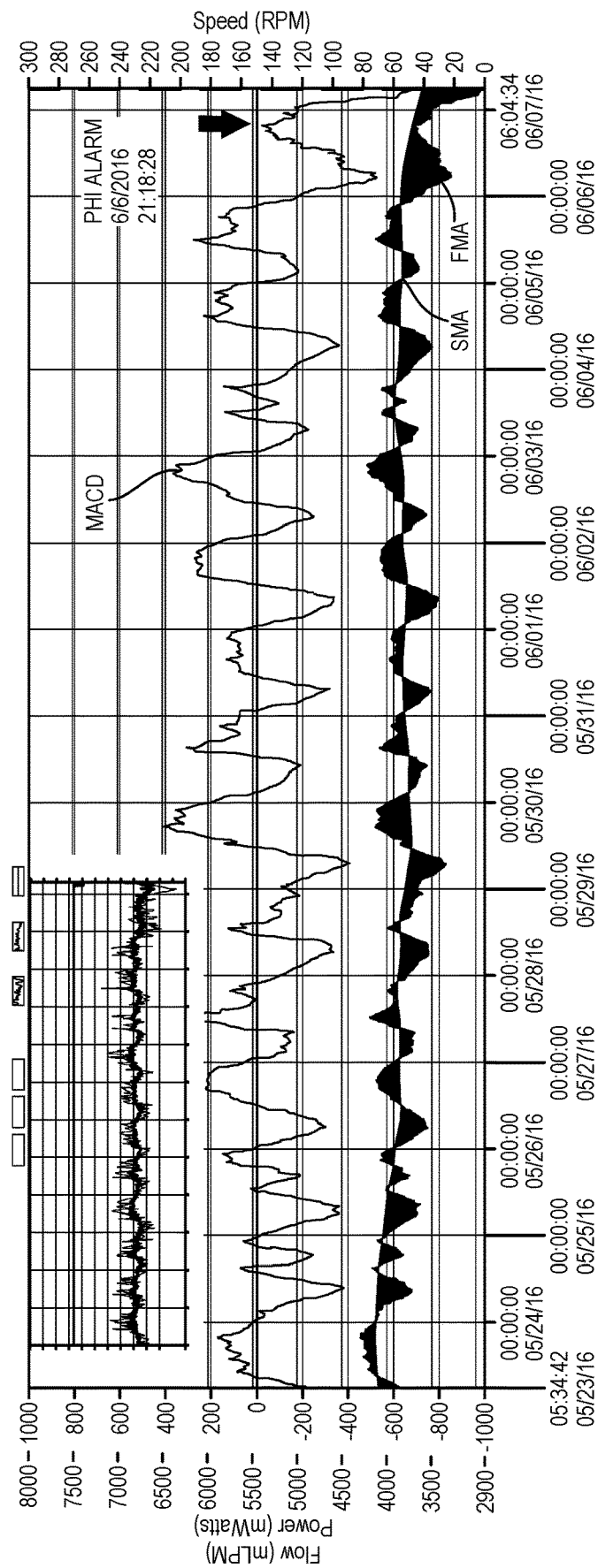
FIG. 6 is an exemplary display of a log file of an implantable blood pump operating in patient with an MACD calculation displayed and indicating the presence of gastrointestinal bleeding.

Referring now to FIG. 6, in this exemplary log file of a patient whose pump is operating is not operating homeostasis, the MACD is displayed above the SMA and FMA trend lines. The original log file is displayed in the upper corner of the log file 12 with the MACD calculations. The MACD does not crosses the zero line between June 6 and June 7 and the MACD exceeds 150% of the maximum or minimum MACD value for the preceding 48 hour period. The alert is generated at the later of those two thresholds. Such an example is indicative of gastrointestinal bleeding as the power decreases substantially to maintain the speed of the impeller. The above described algorithm for detecting trends and outliers is effective at detecting approximately 70% of GI bleeding conditions.

Figure 7:
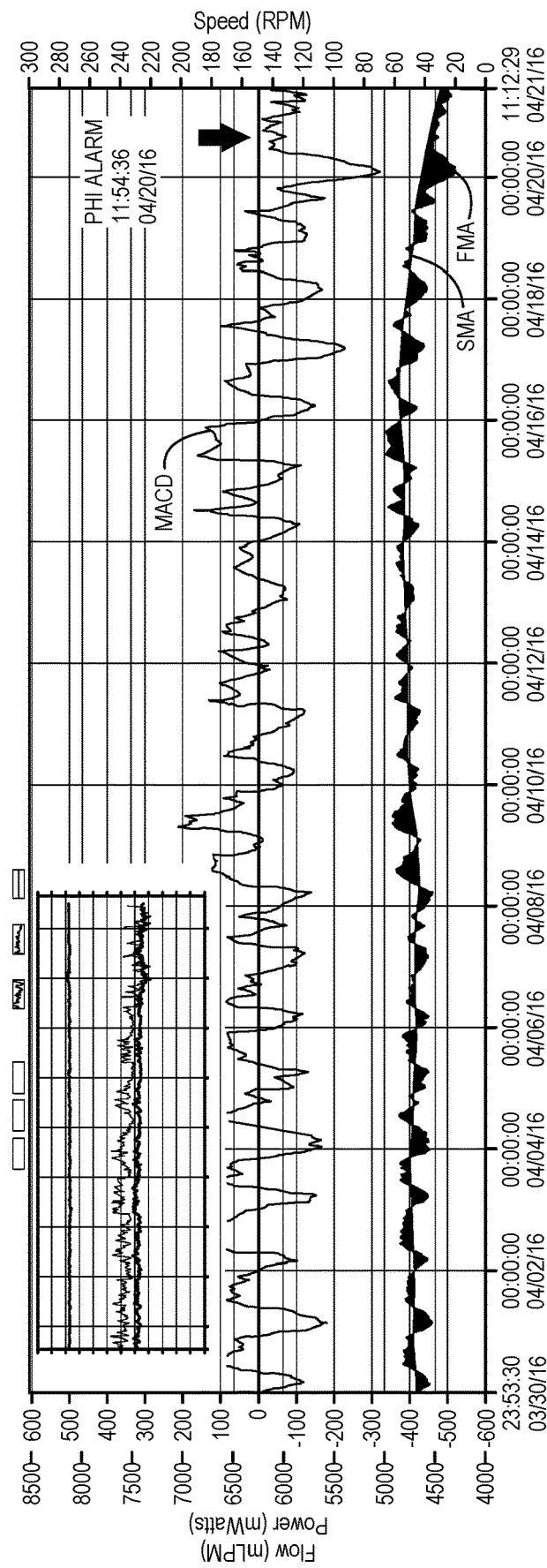
FIG. 7 is an exemplary display of a log file of an implantable blood pump operating in patient with an MACD calculation displayed and indicating the presence of an arrhythmia.

Referring now to FIG. 7, in this exemplary log file 12 of a patient whose pump is operating is not operating homeostasis, the MACD is displayed above the SMA and FMA trend lines. The original log file is displayed in the upper corner of the log file 12 with the MACD calculations. The MACD does not crosses the zero line between just before April 20 and April 21 and the MACD exceeds 150% of the maximum or minimum MACD value for the preceding 48 hour period. The alert is generated at the later of those two thresholds. Such an example is indicative of an arrhythmia as the power fluctuates rapidly to maintain the speed of the impeller. The above described algorithm for detecting trends and outliers is effective at detecting approximately 80% of arrhythmia and tachycardia conditions.

It will be appreciated by persons skilled in the art that the present embodiments are not limited to what has been particularly shown and described herein above. In addition, unless mention was made above to the contrary, it should be noted that all of the accompanying drawings are not to scale.

What is claimed is:

1. A method of determining adverse events from operation of an implantable blood pump, comprising:
   calculating a moving average convergence divergence (MACD) based on power consumed by the implantable blood pump to maintain a constant rotational speed of an impeller of the implantable blood pump; and
   generating an alert when the calculated MACD diverges from a predetermined MACD threshold and exceeds a predetermined MACD zero-crossing time threshold.

2. The method of claim 1, wherein calculating the MACD includes calculating a slow moving average (SMA), and wherein the SMA is an average measurement of the power consumed by the implantable blood pump measured at a predetermined interval for a first predetermined period of time.

3. The method of claim 2, wherein the predetermined interval is 15 minutes.

4. The method of claim 2, wherein the first predetermined period of time is 48 hours.

5. The method of claim 4, wherein calculating the MACD includes calculating a fast moving average (FMA), and wherein the FMA is an average measurement of the power consumed by the implantable blood pump measured at the predetermined interval for a second predetermined period of time less the first period of time.

6. The method of claim 5, wherein the second predetermined period of time is four hours.

7. The method of claim 1, wherein the predetermined MACD threshold is at least one from the group consisting of a minimum MACD value and a maximum MACD value over a continuous 48 hour period multiplied by 150%.

8. The method of claim 1, wherein the predetermined MACD zero-crossing time threshold is 24 hours.

9. The method of claim 1, wherein the alert is generated at a time of the later of the occurrence of:
   when the calculated MACD diverges from the predetermined MACD threshold; and
   when the calculated MACD exceeds the predetermined MACD zero-crossing time threshold.

10. The method of claim 1, wherein the method further includes clearing the alert when the MACD crosses a zero line of the MACD.

11. The method of claim 1, wherein the method further includes calculating a first average power consumed by the implantable blood pump measured at a predetermined interval for a third predetermined period of time;
   calculating a second average power consumed by the implantable blood pump measured at the predetermined interval for a fourth predetermined period of time greater than the first period of time;
   generating the alert when the calculated first average power consumed by the implantable blood pump deviates from the calculated second average power consumed by the implantable blood pump by two standard deviations.

12. The method of claim 11, wherein the third predetermined period of time is three hours.

13. The method of claim 11, wherein the fourth predetermined period of time is five days.

14. The method of claim 11, wherein the method further includes clearing the alert when the first average power consumed by the implantable blood pump converges to the calculated second average power consumed by the implantable blood pump by less than two standard deviations.

15. The method of claim 1, wherein generating the alert is indicative of at least one from the group consisting of thrombus, gastrointestinal bleeding, tachycardia, arrhythmia, and right heart failure.

16. A system for determining adverse events from operation of an implantable blood pump, comprising:
   a controller having a processor, the controller being in communication with the implantable blood pump and a power source configured to provide power to the implantable blood pump, the controller being configured to:
   calculate a moving average convergence divergence (MACD) based on power consumed by the implantable blood pump to maintain a constant rotational speed of an impeller of the implantable blood pump; and
   generate an alert when the calculated MACD diverges from a predetermined MACD threshold.

* * * * *